United States Patent [19]
Boland et al.

[11] Patent Number: 5,893,715
[45] Date of Patent: *Apr. 13, 1999

[54] DENTAL TREATMENT APPARATUS

[75] Inventors: Bernhard Boland, Frankfurt; Georges Driesen, Weilrod; Werner Haczek, Idstein, all of Germany

[73] Assignee: Braun Aktiengesellschaft, Frankfurt, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/841,170

[22] Filed: Apr. 29, 1997

[30] Foreign Application Priority Data

May 3, 1996 [DE] Germany .............. 196 17 638

[51] Int. Cl.⁶ .............. A61C 1/07; A61C 3/03; A61C 3/08
[52] U.S. Cl. .............. 433/118
[58] Field of Search .............. 433/114, 118, 433/122, 125; 601/139, 141, 142; 132/322

[56] References Cited

U.S. PATENT DOCUMENTS

| | | | |
|---|---|---|---|
| 1,354,139 | 9/1920 | Shaw | 433/122 X |
| 2,135,933 | 11/1938 | Blair | 433/122 X |
| 3,149,494 | 9/1964 | Hulse | 433/122 X |
| 3,552,022 | 1/1971 | Axelsson | 433/122 |
| 3,645,255 | 2/1972 | Robinson | 433/119 X |
| 4,110,908 | 9/1978 | Craston | |
| 4,173,828 | 11/1979 | Lustig et al. | 433/122 X |
| 4,544,356 | 10/1985 | Cardella et al. | 433/122 |
| 5,123,841 | 6/1992 | Millner | |
| 5,311,632 | 5/1994 | Center | |
| 5,340,310 | 8/1994 | Bifulk | 433/122 X |

FOREIGN PATENT DOCUMENTS

| | | |
|---|---|---|
| 0 092 861 A1 | 11/1983 | European Pat. Off. . |
| 0 238 778 A2 | 9/1987 | European Pat. Off. . |
| 1 933 355 | 7/1972 | Germany . |
| 26 49 209 A1 | 5/1978 | Germany . |
| 29 49 647 A1 | 6/1981 | Germany . |
| 32 16 564 A1 | 1/1983 | Germany . |
| 34 38 462 C1 | 1/1986 | Germany . |
| 1287552 | 8/1972 | United Kingdom . |
| 2302285 | 1/1997 | United Kingdom . |
| WO85/03632 | 8/1985 | WIPO . |

*Primary Examiner*—Nicholas D. Lucchesi
*Attorney, Agent, or Firm*—Fish & Richardson P.C.

[57] ABSTRACT

The invention is directed to an apparatus for treating the teeth and/or gums. This apparatus includes a treatment tool (1) for removing plaque in particular from the gum margin and/or for stimulating the gingival tissue. The treatment tool (1) is adapted to be set in vibration. For example, it is possible to generate the vibration by an unbalance structure (12) on a drive shaft (7) of the apparatus. The vibration results in a substantial improvement of the tooth cleaning and/or gum stimulating action.

17 Claims, 2 Drawing Sheets

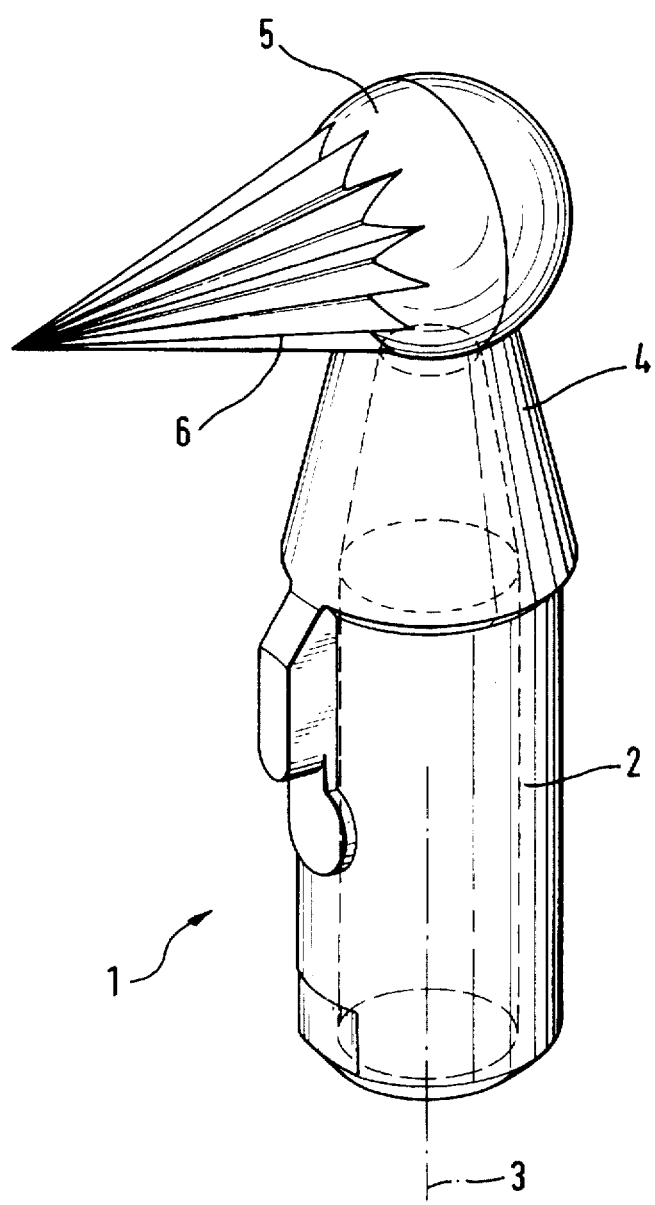
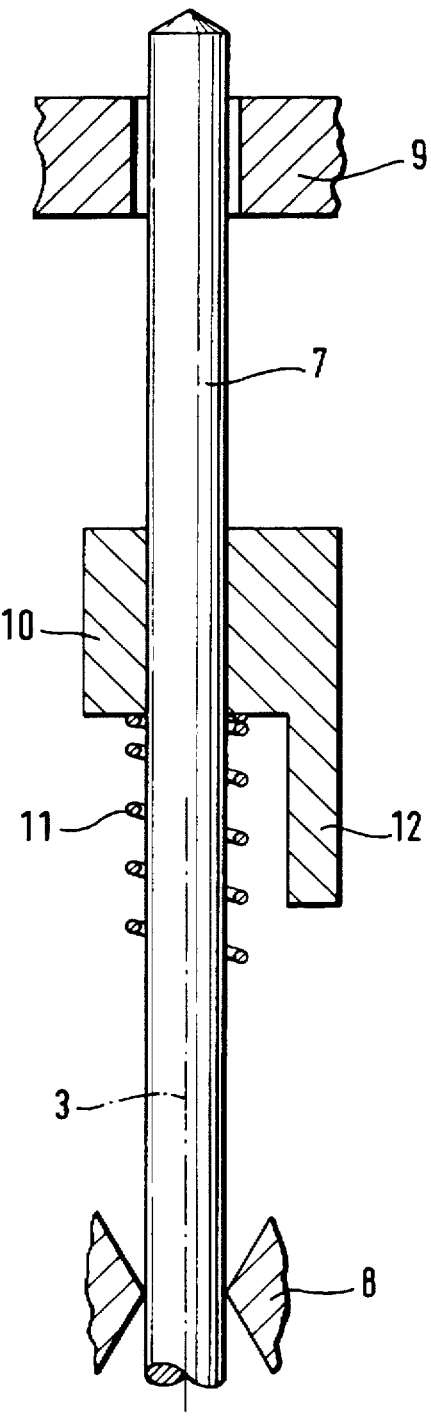
Fig. 1
Fig. 2

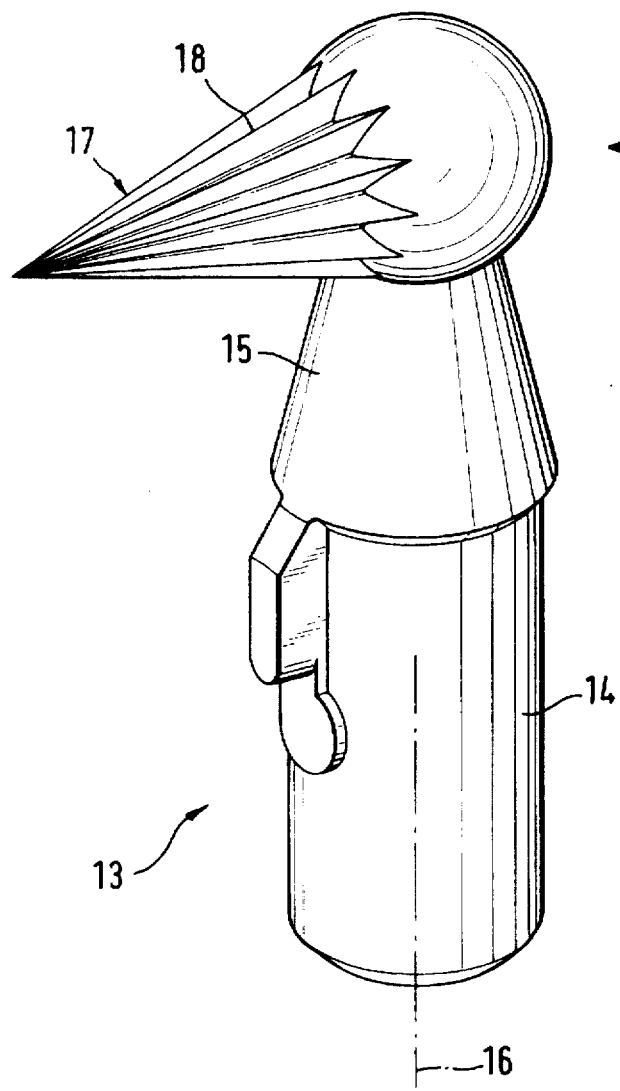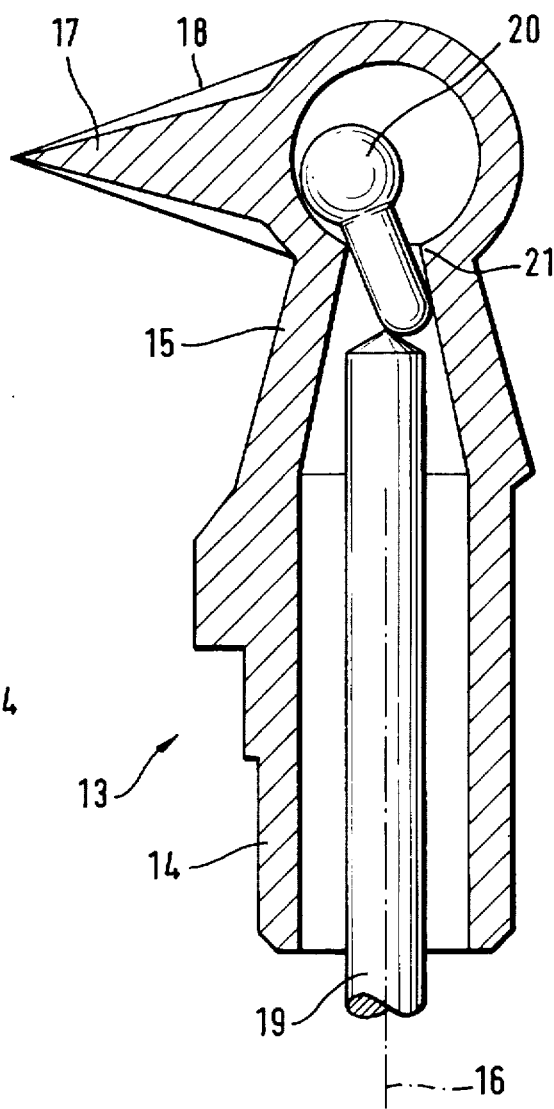
Fig. 3
Fig. 4

5,893,715

DENTAL TREATMENT APPARATUS

This invention relates to an apparatus for treating the teeth and/or gums with a treatment tool for removing plaque in particular from the gum margin and/or for stimulating the gingival tissue.

An apparatus of this type is, for example, a toothbrush-type stem having a rubber tip or the like instead of bristles on its free end. Such apparatuses are used inter alia by dentists and serve on the one hand to clean the teeth, particularly to remove plaque in the tooth-gingiva junction region, and/or on the other hand to stimulate the gingival tissue, meaning to promote blood supply to the gums.

It is an object of the present invention to improve the known apparatus with regard to its cleaning and/or stimulating effect.

According to the present invention, this object is accomplished with an apparatus of the type initially referred to in that the treatment tool is adapted to be set in vibration.

The cleaning of the teeth is improved by the vibration of the treatment tool. Particularly plaque can be removed substantially more easily and thoroughly from the surfaces of the teeth and in particular from the gum margin by means of the vibrating treatment tool. A substantial advantage of the invention is that by virtue of the vibration the plaque separates from the surface of the teeth on its own without the user having to scratch on the surface of the teeth with the treatment tool. Plaque removal thus takes place quasi automatically while the teeth are being gently treated.

Stimulation of the gingival tissue is improved by the vibration of the treatment tool. The vibration stimulates the gingival tissue and promotes the supply of blood to the gums. To this effect it is sufficient for the user to place the treatment tool on the gums. The vibration of the treatment tool is then transmitted automatically to the gums, stimulating the gums in this way.

In an advantageous further aspect of the present invention, electric drive means are provided enabling the treatment tool to be set in vibration. This represents a simple and economical way to generate the vibrations in accordance with the invention. By virtue of their arrangement and/or bearing and/or their other configuration, the electric drive means can cause the attached treatment tool to vibrate even without any additional measures being taken. It is also possible for the electric drive means to be controlled, particularly clocked, for the vibrations to arise. The generated vibrations propagate from the electric drive means via the apparatus itself, for example the housing of the apparatus, and where applicable via further components to the treatment tool. It is not absolutely necessary, therefore, for a direct link to exist between the electric drive means and the treatment tool.

In another advantageous aspect of the present invention the electric drive means include a drive shaft, and means are provided which are coupled with the drive shaft to generate the vibration of the treatment tool. The vibration of the treatment tool is thus generated by means cooperating with the drive shaft. This represents a further simplification with respect to generating the vibration according to the invention. It is not necessary to configure the entire electric drive means in a manner producing the vibration, but it suffices to couple only the drive shaft with the appropriate means in order to generate the vibration. By virtue of its arrangement and/or bearing and/or its other configuration, the drive shaft can thus cause the attached treatment tool to vibrate even without any further measures being taken. Hence the electric drive means can be commercially available items and only the related drive shaft has to be acted upon correspondingly.

In a first advantageous embodiment of the present invention the drive shaft has an unbalance structure generating the vibration of the treatment tool. This is an extremely simple and economical way to generate the vibration according to the invention. The unbalance structure can be a small weight fastened to any point of the drive shaft. It is also possible for the unbalance to be produced by a minor bend in the drive shaft. These are all ways in which an unbalance and hence the vibration of the treatment tool according to the invention can be produced by insubstantial means.

In an advantageous further aspect of the present invention the unbalance structure is fastened to or integrally formed with a component of the drive shaft, particularly a limit stop for the drive shaft. It is no longer necessary, therefore, to provide a separate means to obtain the unbalance, the unbalance structure being quasi integrated already in a component of the drive shaft. Particularly suitably, this component is, for example, a limit stop or the like for the drive shaft. In this case all that is necessary to create the unbalance is an appropriate configuration of this limit stop, which exists already. A further advantage of this further aspect is that the unbalance can be adapted very precisely to the respective requirements. For this purpose, it is necessary only to make the unbalance structure larger or smaller or to arrange it at a larger or smaller distance to the axis of the drive shaft.

In an advantageous further aspect of the present invention the free end of the drive shaft is guided in a bearing whose clearance is greater than usual. As the result, the drive shaft has greater freedom of motion in the bearing than actually necessary and the unbalance is thus able to make itself more strongly felt. In simplified terms it can be said that, because of the greater bearing clearance, the drive shaft is able to oscillate more intensively within the bearing, resulting in a stronger vibration.

In an advantageous further aspect of the present invention the treatment tool has a first part made of a rigid material to transmit the vibration and a second part made of a soft material to treat the teeth and/or gums. By virtue of this two-component construction of the treatment tool, the vibration is transmitted particularly effectively via the rigid material to the soft material. The user can then clean his teeth or stimulate his gums with the soft material.

In a second advantageous embodiment of the present invention, provision is made for a nutating member which is adapted to be set in a nutating rotary motion by the drive shaft and generates the vibration of the treatment tool. The nutating rotary motion of the nutating member effects the vibration. This represents a very effective way to generate the vibration according to the invention. The intensity of the vibration can be varied particularly easily in dependence on the construction of the nutating member, in particular its size and/or weight. A further advantage of this embodiment is that the electric drive means and/or the drive shaft need not be altered but that the desired vibration is generated solely by the nutating member. For its part the nutating member affords ease and economy of manufacture.

In an advantageous further aspect of the present invention the nutating member is accommodated in the interior of the treatment tool so as to be movable therein freely, and the free end of the drive shaft is capable of making contact with the nutating member. By accommodating the nutating member in the interior of the treatment tool there is no need for any provisions whatsoever as regards the holding and bearing or the like of the nutating member. The advantage of this arrangement furthermore is that the nutating rotary motion of the nutating member can act upon the treatment tool directly, meaning that the vibration generated by the nutating motion can act directly on the treatment tool. The feature according to which the free end of the drive shaft can make contact with the nutating member equally means that there is no need for a fixed link between the drive shaft and the nutating member. This has the advantage of enabling the treatment tool with the nutating member accommodated therein to be plugged on and pulled off the complete apparatus for treating the teeth and/or gums without any further measures being required. The only essential point is for there to be sufficient contact between the mentioned components in order to set also the nutating member in rotation when the drive shaft is rotating. This is already the case, for example, simply when the nutating member is able to sit on, or at least touch, the free end of the drive shaft. This can be accomplished extremely easily by an appropriate arrangement and configuration of the nutating member in particular.

In an advantageous further aspect of the present invention, provision is made for a nutation edge along which the nutating member can move. The nutating rotary motion of the nutating member can be influenced by the nutation edge. In particular it is easy with the nutation edge to enhance the nutating motion of the nutating member in a way that results in a substantial intensification of the generated vibration. In turn this enables the nutating member itself to be scaled down in its construction, particularly in its dimensions and/or weight, and the resultant reduction in the generated vibration to be compensated for by means of the nutation edge. The nutation edge thus permits a smaller nutating member and hence a smaller treatment tool to be manufactured to obtain a vibration of at least equal magnitude.

In an advantageous further aspect of the present invention the treatment tool is made in a single piece of a soft material suitable for the treatment of the teeth and/or gums. The treatment tool is thus made of just one component. This represents a substantial advantage in particular as regards the treatment tool's manufacturing cost. Furthermore, the use of only soft material for the treatment tool reliably rules out the user injuring himself on hard components of the treatment tool due to improper handling.

In an advantageous embodiment of the present invention the treatment tool is releasably connectable to a handle section, the electric drive means are accommodated in the handle section, and the drive shaft extends in the direction of the treatment tool. All in all this results in an apparatus which in appearance is already similar to the electric toothbrushes of the art. Furthermore, the treatment tool can be replaced in a manner notable by the user. On the one hand, this may be done after the treatment tool has become worn. On the other hand, the entire apparatus is thus suitable to be used by several users. In this respect, too, the apparatus for treating the teeth and/or gums according to the invention is similar to the electric toothbrushes of the art. As such the apparatus according to the invention is self-explanatory and can be used without further instructions.

In an advantageous embodiment of the present invention the treatment tool has a cleaning tip which is of a conical configuration and has cleaning edges converging radially to the tip. This embodiment of the treatment tool has proven particularly suitable in practice with regard to the removal of plaque in particular from the gum margin by means of the cleaning edges on the one hand, and with regard to the stimulation of gingival tissue by means of the conical form on the other hand.

In an advantageous embodiment of the present invention the treatment tool can be replaced by a cleaning tool which is adapted to be set in rotation by the electric drive means acting via the drive shaft. With this embodiment, it is not only possible to use the complete apparatus according to the invention for tooth and/or gum treatment but it is also possible to equip the apparatus with a replaceable cleaning tool using it, for example, for cleaning the interproximal spaces or the surfaces of the teeth. As cleaning tool it is thus possible to use a cleaning pin, for example, which can be set in rotation by the drive shaft and can be used for cleaning the interproximal spaces. Similarly it is possible to use as cleaning tool a bristle structure which can be set in a rotating or alternating motion by the drive shaft and can then be used for cleaning the surfaces of the teeth. Hence the possibilities of using the apparatus according to the invention are extended substantially by this embodiment.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference. In the drawings, FIG. 1 is a schematic perspective view of a first embodiment of a treatment tool for an apparatus for tooth and/or gum treatment constructed in accordance with the present invention;

FIG. 2 is a schematic view, partly in section, of the drive shaft of the apparatus of FIG. 1 of the present invention;

FIG. 3 is a schematic perspective view of a second embodiment of a treatment tool for an apparatus for tooth and/or gum treatment constructed in accordance with the present invention; and FIG. 4 is a schematic sectional view of the treatment tool of FIG. 3.

In German Offenlegungsschrift DE 43 09 078 A1 there is described an electrically powered dental cleaning apparatus which is hereby incorporated in the disclosure content of the present patent application by express reference in its entirety as well as in respect of its individual features. This dental cleaning apparatus forms the basis for the embodiments of apparatuses for treating the teeth and/or gums according to the present invention, which are described in the following. It will be understood, of course, that any other suitably constructed apparatus can also form such a basis.

In German Offenlegungsschrift DE 43 09 078 A1 there is described a dental cleaning apparatus in which an attachment section is plugged on a handle section. Accommodated in the handle section is an electrically powered motor which can be turned on and off by the user by means of a switch. The attachment section has a plug-on cleaning tool in which a cleaning pin coupled with the motor is displaceably accommodated in a bent sleeve. When the user turns on the motor, the cleaning pin is set in rotation, enabling the user to clean in particular the interproximal areas with the cleaning pin.

FIG. 1 shows a first embodiment of a treatment tool 1 for an apparatus for treating the teeth and/or gums in accordance with the present invention. This treatment tool 1 can be plugged in place of the cleaning tool onto the attachment section of the dental cleaning apparatus disclosed in German Offenlegungsschrift DE 43 09 078 A1. The resulting apparatus then forms the apparatus for treating the teeth and/or gums according to the present invention.

The treatment tool 1 has a shank 2 conforming to the attachment section of the dental cleaning apparatus and suitable for plugging the treatment tool 1 onto the attachment section. The shank 2 is of a cylindrical configuration, tapering on its free end 4 facing away from the attachment section. The central longitudinal axis 3 of the shank 2 is arranged approximately concentrically with the central longitudinal axis of the attachment section. On its free end 4 the shank 2 is equipped with a cleaning tip 5 which projects approximately at right angles to the central longitudinal axis 3. The cleaning tip 5 is of a conical configuration having cleaning edges 6 converging radially to the tip.

While the shank 2 consists of a rigid material, for example SAN, the cleaning tip 5 is made of a soft material, for example thermoplastic. All in all the treatment tool 1 can be manufactured conveniently in a two-component injection molding process.

The shank 2 of the treatment tool 1 is hollow inside. With the treatment tool plugged on the attachment section the drive shaft of the motor may extend into the area of the treatment tool but not necessarily. In either case there is no direct link between the drive shaft and the treatment tool 1. Hence the drive shaft is not under any load, running idle.

This is shown in more detail in FIG. 2. In this Figure, the drive shaft of the motor of the dental cleaning apparatus disclosed in German Offenlegungsschrift DE 43 09 078 A1 is marked with reference numeral 7. This drive shaft 7 extends approximately concentrically with the central longitudinal axis 3 of the shank 2 and hence of the attachment section of the dental cleaning apparatus. The drive shaft 7 does not drive any other component.

The drive shaft 7 is rotatably mounted in a bearing 8 in the interior of the handle section and in a bearing 9 on the free end of the drive shaft 7 and the handle section of the dental cleaning apparatus. Arranged in-between is a limit stop 10 which is fixedly connected with the drive shaft 7. The limit stop 10 serves the function of supporting a spring 11 which always urges the drive shaft 7 back into an initial position.

An unbalance structure 12 is fastened to one side of the limit stop 10 of the drive shaft 7. Furthermore, the bearing 9 has a clearance greater than what would be required for bearing the drive shaft 7. This enables the drive shaft 7 to oscillate more intensively than usual across the central longitudinal axis 3.

With the complete apparatus switched on, the unbalance structure 12 prevents the drive shaft 7 from running true, causing it to oscillate in the bearing 9. This results in a vibration of the drive shaft 7, which propagates to the complete apparatus for treating the teeth and/or gums according to the invention. The vibration is transmitted in particular via the attachment section and the rigid shank 2 of the treatment tool 1 to the soft cleaning tip 5.

By means of this vibration transmitted to the cleaning tip 5 the user is able, on the one hand, to clean his teeth in particular in the gumline area and/or, on the other hand, to stimulate his gingival tissue, thus promoting blood supply to the gums. The removal of plaque is promoted in particular by the cleaning edges 6 of the cleaning tip 5, while the soft material of the cleaning tip 5 in particular is beneficial in stimulating the gingival tissue.

FIG. 3 shows a second embodiment of a treatment tool 13 for an apparatus for treating the teeth and/or gums according to the invention. This treatment tool 13 can be plugged in place of the cleaning tool onto the attachment section of the dental cleaning apparatus disclosed in German Offenlegungsschrift DE 43 09 078 A1. The resulting apparatus then forms the apparatus for treating the teeth and/or gums according to the present invention.

The treatment tool 13 has a shank 14 which conforms to the attachment section of the dental cleaning apparatus and is suitable for plugging the treatment tool 13 onto the attachment section. The shank 14 is of a cylindrical configuration, tapering on its free end 15 facing away from the attachment section. The central longitudinal axis 16 of the shank 14 is arranged approximately concentrically with the central longitudinal axis of the attachment section. On its free end 15 the shank 14 is equipped with a cleaning tip 17 which projects approximately at right angles to the central longitudinal axis 16. The cleaning tip 17 is of a conical configuration and has cleaning edges 18 converging radially to the tip.

The complete treatment tool 13 is made in a single piece of a soft material suitable to treat the teeth and/or gums. The treatment tool 13 is made in particular of Hytrel.

A cross section of the treatment tool 13 is shown in FIG. 4. In this Figure, the drive shaft of the motor of the dental cleaning apparatus disclosed in German Offenlegungsschrift DE 43 09 078 A1 is marked with reference numeral 19. This drive shaft 19 extends approximately concentrically with the central longitudinal axis 15 of the shank 14 and hence of the attachment section of the dental cleaning apparatus.

The treatment tool 13 is hollow inside. The drive shaft 19 extends into the interior of the treatment tool 13. Accommodated therein furthermore is a nutating member 20 which is constructed in rotationally symmetric shape and has a spherical form on its end facing away from the drive shaft 19. The nutating member 20 is made of a heavy material, in particular steel.

In its interior the treatment tool 13 has a nutation edge 21 which is arranged in the area of the nutating member 20 and serves to guide the nutating member 20. The nutation edge 21 has a diameter greater than the outer diameter of the nutating member 20. Otherwise the nutating member 20 is free to move inside the treatment tool 13.

The drive shaft 19 and the nutating member 20 are constructed and arranged relative to each other so that the free end of the drive shaft 19 is able to come into contact with the nutating member 20. In particular the free end of the drive shaft 19 makes contact with the free end of the nutating member 20 facing away from the spherical form.

With the complete apparatus switched on, the contact between the drive shaft 19 and the nutating member 20 results in the rotary motion of the drive shaft 19 being transmitted at least partly to the nutating member 20. Because the nutating member 20 is free to move in the interior of the treatment tool 13, the nutating member 20 is set in a nutating rotary motion. This means that the nutating member 20 rotates approximately about its longitudinal axis while at the same time it nutates approximately about a transverse axis.

The nutating member 20 moves along the nutation edge 21 and, because of the greater diameter of the nutation edge 21, is disturbed in its rotary motion and is set in a nutating motion Hence the nutating rotary motion is further promoted and intensified by the nutation edge 21.

All in all the nutating motion of the nutating member 20 inside the treatment tool 13 results in the treatment tool 13 being set in vibration. Through the physical proximity of the nutating member 20, the cleaning tip 17 in particular is made to vibrate.

By means of this vibration acting on the cleaning tip 17, a user is able, on the one hand, to clean his teeth in particular in the gumline area and/or, on the other hand, to stimulate his gingival tissue, meaning to promote the blood supply to the gums. The removal of plaque is promoted in particular by the cleaning edges 18 of the cleaning tip 17, while the soft material of the cleaning tip 17 in particular is beneficial in stimulating the gingival tissue.

It will be understood, of course, that the two above described embodiments can also be used in combination. In a third embodiment of this type the drive shaft then has an unbalance and there is also a nutating member. It is thus possible to generate an even more intensive vibration of the treatment tool and in particular of the cleaning tip, resulting in even more effective cleaning of the teeth and/or stimulation of the gums.

We claim:

1. An apparatus for treating the teeth and/or gums, comprising:

a one-piece unitary treatment tool slaving a shank and a cleaning tip for removing plaque from the gum margin and/or for stimulating the gingival tissue, wherein said cleaning tip extends from said shank, said cleaning tip being made of a material softer than the shank; and an electric drive unit to which the shank couples, said electric drive unit during operation causing the treatment tool to vibrate, wherein the vibration is transferred from the electric drive unit through the shank to the cleaning tip.

2. The apparatus as claimed in claim 1, wherein the electric drive unit is releasably coupled to the treatment tool.

3. The apparatus as claimed in claim 1, the electric drive unit further comprising a drive shaft which rotates during operation, and a component which is in contact with the drive shaft to generate the vibration of the treatment tool.

4. The apparatus as claimed in claim 3, wherein said component is an unbalance structure coupled to the drive shaft and which during operation causes the drive shaft to vibrate.

5. The apparatus as claimed in claim 4, wherein the unbalance structure is fastened to or integrally formed with a component of the drive shaft.

6. The apparatus as claimed in claim 4, wherein the drive unit further comprises a guide bearing having loose tolerances guiding a free end of the drive shaft.

7. The apparatus as claimed in claim 1, further comprising a handle section and wherein the treatment tool is releasably connectable to the handle section, the electric drive unit is accommodated in the handle section, and the drive shaft extends in the direction of the treatment tool.

8. The apparatus as claimed in claim 1, wherein the treatment tool has a cleaning tip which is of a conical configuration and has cleaning edges converging radially to a point.

9. An apparatus for treating the teeth and/or gums, comprising:

an electric drive unit including a drive shaft which rotates during operation; and a treatment tool for removing plaque from the gum margin and/or for stimulating the gingival tissue, the treatment tool comprising a body and a nutating member contained and freely movable within an interior space formed inside said body, said nutating member remaining with treatment tool when the treatment tool is removed from the drive unit, wherein said nutating member is set in a nutating rotary motion inside said interior space through contact with the rotating drive shaft and causes the treatment tool to vibrate.

10. The apparatus as claimed in claim 9, wherein the nutating member accommodated in and interior of the treatment tool so as to be movable therein freely, and a free end of the drive shaft, during operation of the drive unit, makes contact with the nutating member.

11. The apparatus as claimed in claim 9, wherein the interior space has a nutation edge along which the nutating member moves during operation.

12. The apparatus as claimed in claim 9, wherein the treatment tool is made in a single piece of a soft material suitable for the teeth and/or gums.

13. The apparatus as claimed in claim 9, further comprising a handle section and wherein the treatment tool is releasably connectable to the handle section, the electric drive unit is accommodated in the handle section, and the drive shaft extends in the direction of the treatment tool.

14. The apparatus as claimed in claim 9, wherein the treatment tool has a cleaning tip which is of a conical configuration and has cleaning edges converging radically to a point.

15. The apparatus as claimed in claim 9, wherein the single piece of soft material comprises a thermoplastic.

16. The apparatus as claimed in claim 9, wherein the single piece of soft material is HYTREL.

17. A one-piece unitary treatment tool comprising:

a shank made of a rigid material; and a cleaning tip extending from the shank and made of a material softer than the shank, wherein the shank comprises means for connecting the shank to an electric drive unit, which during operation causes the treatment tool to vibrate, and wherein vibration is transferred from the electric drive unit through the shank to the cleaning tip.

* * * * *